United States Patent [19]
Dorsey, III

[11] Patent Number: 5,522,796
[45] Date of Patent: * Jun. 4, 1996

[54] METERING GAUGE TRUMPET VALVE

[75] Inventor: James H. Dorsey, III, Delray Beach, Fla.

[73] Assignee: C.R. Bard, Inc., Murray Hill, N.J.

[ * ] Notice: The term of this patent shall not extend beyond the expiration date of Pat. No. 5,303,735.

[21] Appl. No.: 139,948

[22] Filed: Oct. 21, 1993

Related U.S. Application Data

[63] Continuation-in-part of Ser. No. 20,062, Feb. 19, 1993, Pat. No. 5,391,145, which is a continuation-in-part of Ser. No. 470,771, Jan. 26, 1990, Pat. No. 5,188,591.

[51] Int. Cl.$^6$ .................................................. A61M 1/00
[52] U.S. Cl. ..................... 604/118; 604/33; 604/249; 251/325; 251/205; 137/596.2
[58] Field of Search ............................ 604/27–35, 38–40, 604/43, 118, 119, 121, 128, 173, 246, 249, 902, 256, 258; 91/454; 137/596, 596.2, 883; 251/325, 205, 253, 256; 128/4 A; 600/156, 159

[56] References Cited

U.S. PATENT DOCUMENTS

| 693,865 | 2/1902 | Huck . | |
|---|---|---|---|
| 807,309 | 12/1905 | Ott | 251/253 |
| 1,059,753 | 4/1913 | O'Brien | 251/325 |
| 1,147,157 | 7/1915 | Foster | 251/325 |
| 1,156,010 | 10/1915 | Kenney . | |
| 1,436,650 | 11/1922 | Gilbert . | |
| 1,740,602 | 12/1929 | Keeler . | |
| 2,698,160 | 12/1954 | Hansen . | |
| 3,192,952 | 7/1965 | Botnick . | |
| 3,231,236 | 1/1966 | Hodel et al. . | |
| 3,473,783 | 10/1969 | Self | 251/325 |
| 4,134,573 | 1/1979 | Messinger . | |
| 4,634,434 | 1/1987 | Marino, Jr. et al. | 604/246 |
| 5,090,450 | 2/1992 | Pelech et al. | 251/325 |
| 5,279,593 | 1/1994 | Hiltebrandt | 604/264 |
| 5,303,735 | 4/1994 | Cerola et al. | 251/205 |
| 5,348,555 | 9/1994 | Zinnanti | 604/33 |

Primary Examiner—C. Fred Rosenbaum
Assistant Examiner—Mark Bockelman
Attorney, Agent, or Firm—Darby & Darby

[57] ABSTRACT

A control valve assembly is disclosed having a housing defining at least one valve chamber having an elongated cylinder. A piston is partially disposed within said valve chamber and the valve assembly allows for reciprocating movement of the piston within said valve chamber. A metering device is provided for precise positioning of the piston within the valve chamber.

13 Claims, 3 Drawing Sheets

5,522,796

METERING GAUGE TRUMPET VALVE

This application is a continuation in part of application Ser. No. 08/020,062, filed Feb. 19, 1993, now U.S. Pat. No. 5,391,145, which is a continuation in part of application Ser. No. 07/470,771, filed Jan. 26, 1990, now U.S. Pat. No. 5,188,591, issued Feb. 23, 1993.

BACKGROUND OF THE INVENTION

1. Field of the Invention

This invention relates generally to the field of laparoscopic surgery and more specifically to a laparoscopic suction/irrigation valve. This valve incorporates a metering feature which is incorporated into the suction valve mechanism of the valve and is used for maintaining clear visibility in the operative field free from laser plume and/or smoke associated with laser and/or electrosurgical procedures.

2. Description of the Prior Art

The increasing use of laparoscopic surgical techniques for performance of a variety of surgical procedures have presented the clinician/surgeon with both new opportunities and new challenges. Where, as in the past, the abdominal cavity was exposed by relatively large incisions, the laparoscopic surgical technique permits access to the surgical site through relatively small incisions referred to as puncture sites through which trocars are inserted. In practice the abdominal cavity remains "closed", inflated however by positive pressure thus distending the abdominal cavity to allow the surgeon access to one or more tissues and/or allows him to relocate lower intestine and/or bowel to reveal other areas within the cavity. Where in the course of the laser procedure and/or electro-surgical procedure, a target tissue is vaporized, electrosurgically cut, or cauterized. The generation of plume and/or smoke and gases are within the confines of the abdominal cavity is produced that will obscure the surgeon's view of the operative field as seen through the imaging bundle of the laparoscope. In such event, the operative procedure is delayed unless or until the obscuring smoke is suctioned by manual depression of the suction button or evacuated by venting the abdominal cavity through a controlled bleed of gas. Such venting has been typically accomplished through a stop cock valve, which is an integral part of a trocar, which is inserted and positioned through the abdominal cavity. This venting allows gas with smoke and plume to exit the abdominal cavity and escape into the operating theater. As smoke is hazardous and can contain airborne pathogens, viruses and toxic gases, this venting is hazardous to the operating room personnel and also a direct violation of proper operating room protocol.

The surgeon is therefore required to evacuate such gas by consciously applying (periodically) suction through a suction/irrigation probe. The surgeon must, thus, divert his effort from other functions and divide his time between performing the surgical procedure and the periodic activation or continuous application of the suction function through the suction irrigation probe, the amount and duration being determined empirically. Where the surgeon is required to perform such clearance of the operative field, his attention is obviously diverted from the task at hand, the operative procedure prolonged and the patient exposed to increasing risk. As is further apparent, the surgeon's ability to efficiently evacuate the plume and/or smoke is, at best, based upon imperfect balancing of the amount of suction, relative to the pressure of the insufflation apparatus. Many times the positive pressure inflation of the abdominal cavity (pneumoperitoneum) is loss and time is wasted while the operation room staff waits for the pneumoperitoneum to again be established.

As is apparent from the foregoing discussion, the increase in the use of laser and/or electro-surgery for localized removal and/or cauterization of tissue within the abdominal cavity has been limited by the plume/cloud which is produced upon vaporization of tissue within the operative field. Unless and until such visually limiting smoke/plume can be dissipated and/or evacuated effectively from the field, the field of view is obscured and the surgical procedure is prolonged and the patient forced to endure unnecessary discomfort/risk. The techniques adopted heretofore for addressing this problem have been generally inadequate for reasons set forth above. Accordingly, there is and remains a continuing need to provide both an improved instrument and technique to effect metered and/or rapid evacuation of gas/smoke from the operative field in a manner which permits essentially uninterrupted performance of the surgical procedure associated therewith. It is, therefore, to the effective resolution of the aforementioned problems and shortcomings that the present invention is directed.

SUMMARY OF THE INVENTION

The present invention relates to an improved valve which incorporates a pair of piston activated valve chambers. The first valve chamber being capable of operative connection to a source of negative pressure and the second valve chamber being capable of operative connection to a source of pressurized fluid. One or both of the foregoing valve chambers is further provided with a metering system which incorporates a unique means for maintaining precise and controlled depression of the piston a fixed amount which can be incrementally increased, effecting the opening of the suction valve and maintaining the valve at the desired setting (open position). The metering system is incorporated into the suction valve and is associated with the piston and valve chamber of this function both operating in conjunction with one another.

In endoscopic surgical procedures wherein laser surgery and/or electro surgery are employed, tissue is routinely vaporized or cauterized resulting in a plume or cloud of vapor which obscures the operative field., This plume or cloud must be removed/evacuated from the abdominal cavity in order to permit the user to continue the operative procedure. Accordingly, the present invention provides for continuous precisely metered adjustable suction and allows for depression of the suction button without interference. Upon return of the suction button from is manually depressed state, it returns to the preset position. This smoke evacuation function is achieved through the use of the metering device/system described above, and in association with the valve chamber/piston associated with the source of negative pressure (suction). The degree of incremental depression can be correlated to an indexing system with settings (protrusion on the valve body in this manifestation) and, thus, the surgeon can select the degree/extent of suction which is applied through a detachable interchangeable probe mounted to the valve body and thereby effect evacuation of smoke and gases from the operative field. Thus, the user is free to manipulate other instrumentation or the probe without having to provide manual continual depression of the suction button, since he or she need not maintain continuous depression of the piston with the suction valve in order to maintain continuous metered suction.

Accordingly, it is an object of the present invention to provide a valve uniquely adapted for providing continuous suction of smoke and gases from an operative field concurrent with insulflation thereof.

It is another object of the present invention to provide a trumpet valve adapted for metered/incremental suction of smoke and gases from an operative field concurrent with insulflation thereof by setting the amount of suction on the trumpet valve thereby freeing the user from continuous attendance of manual operation of the suction function.

Other objects and advantages of this invention will become apparent from the following description taken in conjunction with the accompanying drawings wherein set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

The invention may be better understood by reference to the drawings in which.

DETAILED DESCRIPTION OF THE INVENTION

Figure 1:
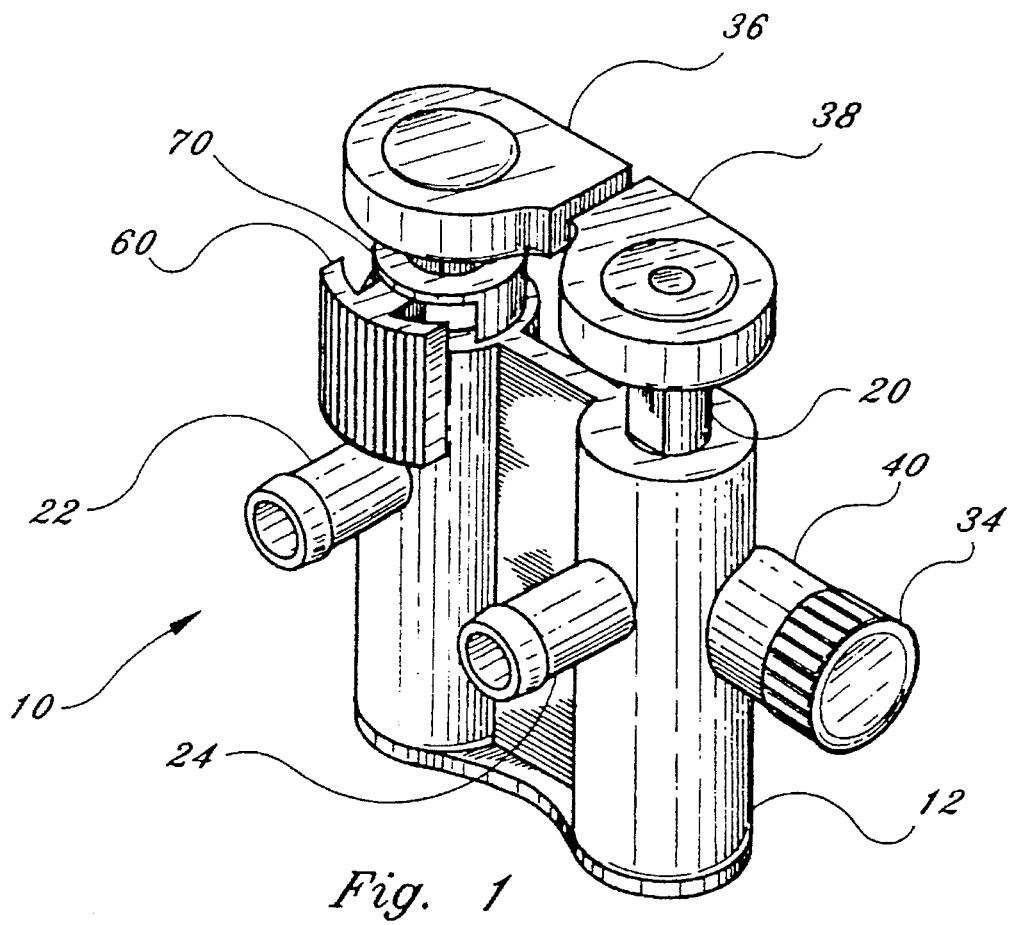
FIG. 1 is a perspective view of a metering gauge trumpet valve in accordance with the present invention.
Figure 2:
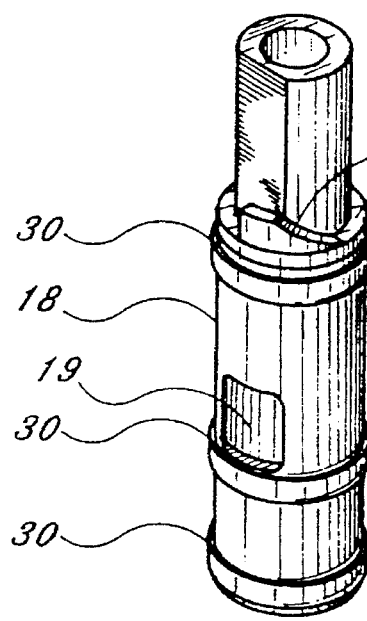
FIG. 2 is a perspective view of the piston and gear combination in accordance with the present invention.
Figure 3:
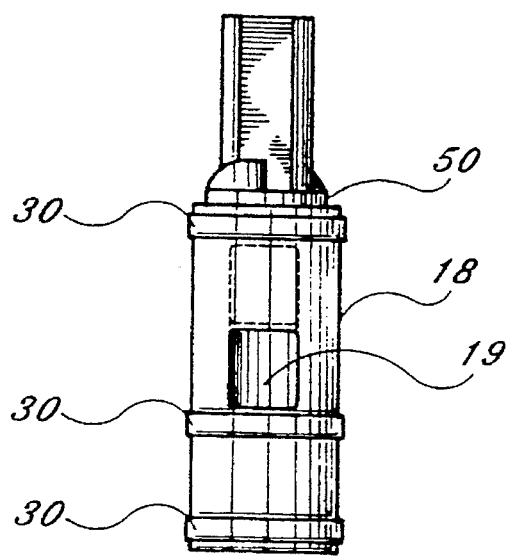
FIG. 3 is a front view of the piston and gear of FIG. 2.

FIGS. 1 illustrates the valve 10 of the present invention. Preferably, valve 10 is a symmetrical trumpet valve, however, the present invention is not limited to such design for the valve. In the preferred embodiment, the valve consists of a valve housing or body 12 which defines a pair of valve chamber 14 and 16 adapted for reciprocating movement of a pair of pistons 18 and 20. The basic operation of the valve is essentially the same as set forth in the U.S. Pat. No. 5,188,591 which is incorporated by reference herein. Valve 10 is initially connected to a source of pressurized fluid and to a source of negative pressure via a pair of fittings 22 and 24 which extend from valve body 12. Additionally, the user mounts an interchangeable probe (not shown) onto either one of two end adapters 40 on valve body 12. Once valve 10 is assembled and connected to the pressurized source of fluid and negative pressure through fittings 22 and 24 it is ready for use. Typically valve 10 is used for suction and irrigation and other various uses such as hydrodissection via pressurized fluids of tissue planes or in conjunction with other laparoscopic instruments to perform various types of infusion of irrigation fluid to clear the operative field and thereby allow for free and unobstructive access and view.

In operation or use of valve 10, the user typically sequentially depresses one piston and then the other to first infuse fluid into the operative field and thereafter suction fluid from the operative field. Pistons 18 and 20 are maintained in a "closed" position by a spring 26 and 28, respectively, or its equivalent located at the bottom of the valve chambers 14 and 16, respectively. The user is thus required to maintain pressure on the piston in order to effect the specific operation provided thereby. When the user releases pressure to the piston, the spring resistance in the valve returns the piston to the closed position.

Thus, the basic structure of valve 10 comprises a housing or valve body 12 defining at least one pair of valve chambers 14 and 16, each of which adapted for reciprocal movement of a piston 18 and 20, respectively. Pistons 18 and 20 are maintained within their corresponding chambers by cap or buttons 36 and 38, respectively, removeably attached to the top of the piston and by a base member removeably attached to the bottom of the valve chambers. This prevents inadvertent removal or displacement of the piston relative to its corresponding valve chamber and the housing. As stated above, pistons 18 and 20 are maintained under spring tension in a closed position. Upon depression of the piston, a passage is provided from one of the fittings 22 or 24, through aperture 19 of the piston for communication with a common channel 40 within valve body 12. Thus, fluid communication is established to either the fitting connected to a source of negative pressure or to the fitting connected to a source of irrigation fluid.

The range of movement off the piston within the chamber is only limited by the amount of pressure applied by the user and the range of movement allowed by the valve chamber of the piston. To the extent the user desires to utilize less than the available amount of irrigation fluid, or negative pressure (suction), the piston is only partially depressed. As is evident, the less than full opening of the valve requires the user to modulate the pressure applied to the piston to achieve the desired effect. To overcome this pressure the present invention provides for a metering means or system which allows the user to depress or displace the piston a precise distance to open the valve and maintain the valve at such setting.

The metering means may be associated with either one or both of the pistons to allow the user to depress or displace the piston incrementally within a limited range of movement of the piston or to a pre-set position within a limited range of movement of the piston. While such metering arrangement is preferably used in association with the piston and valve chamber associated with connection to a source of negative pressure, the metering means can be use or associated with either or both of the valve chambers.

When the valve 10 is closed, the piston 18 or 20 is in its uppermost position within the valve chamber 14 or 16, respectively, to effect proper sealing of the valve chamber and thereby prevent the valve from leaking (the inadvertent infusion of fluid or application of negative pressure through the probe mounted to the valve body 12). When the user desires to actuate valve 10, he or she simply depresses the piston either partially or totally, depending upon his or her requirements and the stage of the procedure involved. As noted above, when pressure upon the piston is released the valve will close automatically due to the pressure of spring 26 or 28 upon the piston from the bottom of the valve chamber 14 or 26, respectively.

Figures 9, 10, 11:
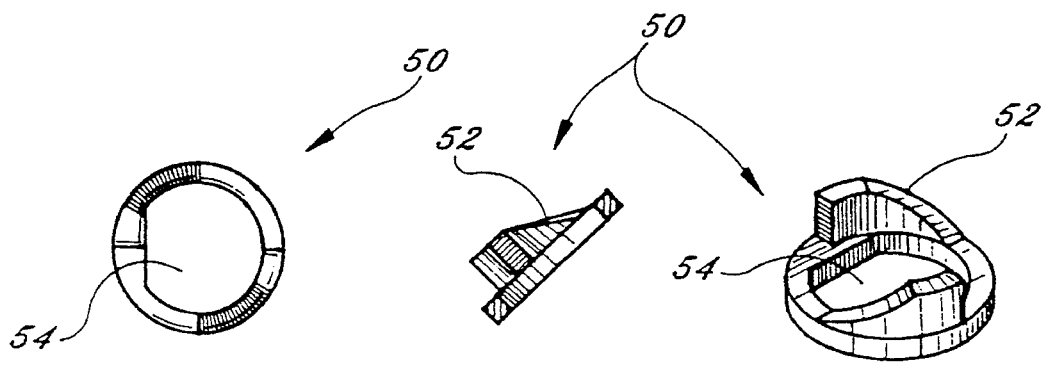
FIG. 9 is a top view of the gear of FIG. 2.
FIG. 10 is a side view of the gear of the gear of FIG. 9.
FIG. 11 is a perspective of the gear of FIG. 9.

The metering means of the present invention is provided and incorporated into valve 10 to effect depression of piston 18 or 20 to the extent necessary to open the valve and maintain the piston in such position. The metering means is preferably associated with piston 18 or 20 and its corresponding valve chamber 14 or 16, respectively. Additionally, two metering means can be incorporated into valve 10, one for each of the pistons. Generally, the metering means is comprised of a gear 50, knob 60 and a member 70 protruding upward from the top of valve body 12 above one of the valve chambers 14 or 16. As seen in FIGS. 9 through 11, gear 50 is essentially circular in shape and contains an aperture 54 extending therethrough and ramp portions 52. In use, the top of piston 18 or 20 is inserted through aperture 54 until gear 50 is resting along the shoulder 21 of piston 18 or 20.

Figure 4:
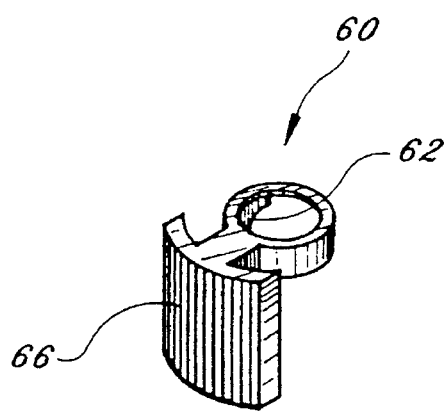
FIG. 4 is a perspective view of the knob in accordance with the present invention.
Figure 6:
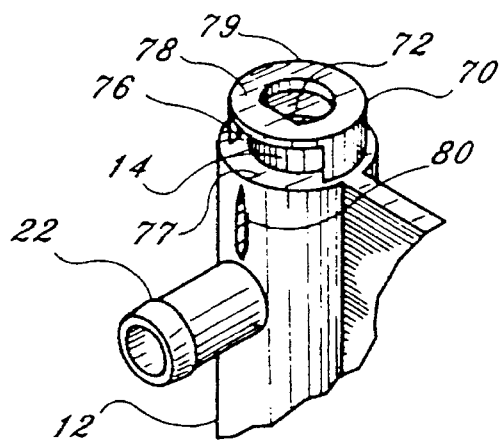
FIG. 6 is a perspective view of a portion of the trumpet valve of FIG. 1.
Figure 5:
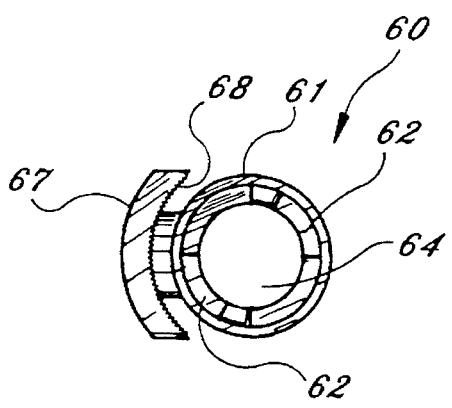
FIG. 5 is a bottom view of the knob of FIG. 4.
Figure 7:
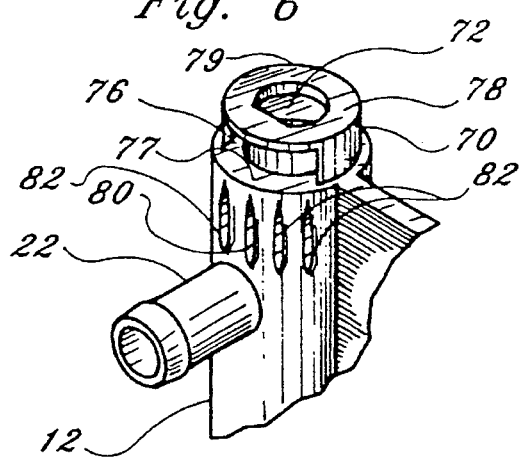
FIG. 7 is a perspective view of a portion of an alternative embodiment of the trumpet valve.

As seen in FIGS. 4 and 5, knob 60 is comprised of a circular portion 61 and a activating lever/pad 66. Lever/pad 66 has serrations or ridges 68 on its inner surface for use in conjunction with a protrusion 80 as will discussed below. Also as seen in FIG. 7, a plurality of protrusions 80 may be provided in lieu of the single protrusion to ensure an accurate and precise measurement of suction bleed. The outer surface of lever/pad 66 can be provided with a gripping surface 67, such as ridges or serrations, to provide a tactile feel when advancing or retracting handle portion 66 along is axis of rotation. Circular portion 61 is similar in construction to gear member 50 and is provided with an aperture 64 extending therethrough and ramp portions 62. As will be discussed below, ramp portions 52 and 62 work against each other to provide precision retraction or extension of piston 18 or 20 within valve chamber 14 or 16, respectively.

Protruding member 70 is generally cylindrical in shape and contains an aperture 72 extending therethrough for receiving the top portion of piston 18 or 20. A portion 76 of the cylindrical sidewall of member 70 is removed or cutout for receiving the circular portion 61 of knob 60, discussed below. In the preferred embodiment, member 70 is permanently attached to valve body 12 above either or both valve chambers 14 and 16.

The top of piston 18 or 20 is inserted into aperture 54 of gear 50, until the bottom surface of gear 50 is flush with shoulder 21 of piston 18 or 20. The circular portion 61 of knob 60 is inserted into the protruding member 70 through cutout portion 76 until the circular portion 61 abuts the inner surface of the sidewall of member 70. Once inserted, circular portion 61 rest along the shoulder 77 of the valve chamber 14 and serrations 68 are operatively associated with the protrusion 80 of valve body 12. Furthermore, the opening at the top of valve chamber 14, opening 64 of knob 60 and aperture 72 of protruding member 70 are aligned with each other for receiving the top portion of piston 18.

A notch 25 is provided on the top portion of piston 18 or 20 to ensure proper alignment of gear 50 when the piston is inserted through gear 50. Opening 54 of gear 50 is shaped in accordance with notch 25 to further ensure proper alignment of gear 50 on piston 18 or 20. Opening 72 of protruding member 70 is shaped similar to aperture 54 of gear 50. The shape of opening 72 in conjunction with notch 25 allows for proper positioning or alignment of pistons 18 within valve chamber 14 to ensure that aperture 19 of piston 18 allows for fluid communication between fitting 22 and conduit 40 when the valve is open. Thus, piston 18, having gear 50 properly aligned and resting upon shoulder 21, is inserted through the opening in the top of valve chamber 14 and opening 72 until ramps 52 of gear 50 and ramps 62 of knob 60 are abutting. Notch 25 in conjunction with the shape of opening 72 ensure that piston 18 is properly aligned within valve chamber 14. Once fully inserted, cap or button 36 is placed on the top of piston 18 and spring 26 is inserted within the bottom of valve chamber 14. Base member 32 ensures that spring 26, as well as spring 28 associated with the non-metering chamber, remain within their associated valve chambers, by closing or sealing off the bottom of valve body 12.

In operation of the metering means, the user advances knob 60 along its axis so as to cause knob ramp 62 to move relative to gear ramp 52. Such relative movement causes the piston 18 or 20 to be partially depressed, thereby slowly opening the valve. The user may also retract knob 60 along its axis to slowly close the valve. The extent to which the valve is opened or closed can be readily determined by the use of an indicating protrusion 80 in conjunction with serrations 68 disposed on the inner surface of the handle portion 66 of knob 60. Each time a serration 68 passes over protrusion 80 a click is made. Each click will correspond to a certain amount of suction bleed, i.e. one click=2 liters suction bleed per minute, two clicks=4 liters suction bleed per minute, etc.

In addition to the metering means, the piston 18 or 20 associated with such metering means, can still be fully depressed by the user without the use of the metering means. The piston associated with the metering means is fully depressed when the cap 36 of such piston is resting upon top surface 79 of protruding member 70.

Thus, the degree of incremental depression of the piston can be correlated with index settings and outflows exactly on the valve body 12 and the user can select the degree and extent of suction which is applied to the unit, thereby effecting evacuation of the proper amount of $CO_2$ and smoke from the operative field correlating to his or her needs and equipment. The user is free to manipulate instruments and not required to intermittently press the suction button in order to actuate and control suction and improve vision.

Figure 8:
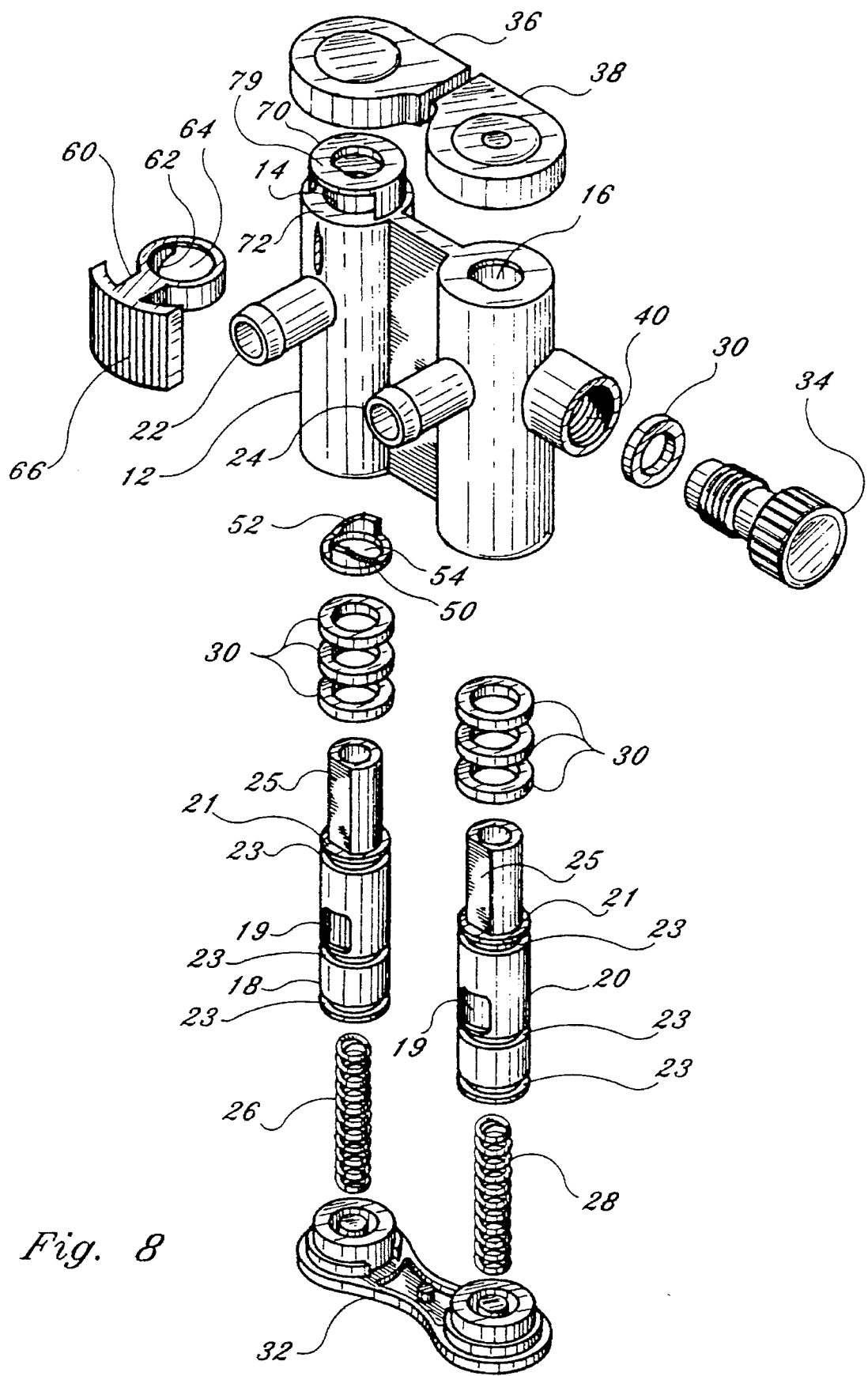
FIG. 8 is an exploded view of the metering gauge trumpet valve of FIG. 1.

FIG. 8 illustrates the various components of a symmetrical trumpet valve 10 having the metering system associated with one of its chambers 14. The valve consists of a valve body 12, caps 36 and 38, O-rings 30, plug 34, knob 60, gear 50, pistons 18 and 20, springs 26 and 28 and base 32. Valve body 12 includes fittings 22 and 24, common conduit 40, valve chambers 14 and 16, protrusion 80 and protruding member 70.

In the construction of the valve, O-rings 30 are placed within grooves 23 on pistons 18 and 20 and on a groove (not shown) on plug 34. A drop of lubrication (not shown) can be added to each O-rings, wherein the pistons are wiped with the lubrication. A drop of lubrication is added to gear 50 which is slipped over the top portion of the vacuum or suction piston 18 until gear 50 rests upon shoulder 21 of piston 18. Pistons 18 and 20 are inserted into their respective chambers 14 and 16, respectively. Knob 60 is inserted within protruding member 70 through opening 76. Once knob 60 is inserted, pistons 18 and 20 are pushed through the openings in the top of valve chambers 14 and 16, and piston 18 is further pushed through opening 62 of knob 60 and opening 72 of protruding member 70. A drop of lubricant is added to springs 26 and 28 and the springs are inserted within the bottom of pistons 18 and 20, respectively. Base 32 is provided to cap the bottom of valve body 12 and ultrasonically welded. Vacuum button or cap 36 and irrigation button or cap 38 are attached to pistons 18 and 20, respectively, with one drop of adhesive each. Lastly, plug 34 is screwed into one end of common conduit 40.

The metering system described above provides for incremental increase or decrease in the valve opening depending upon the changing conditions of the operative procedure, over the full range of piston displacement afforded by ramps 52 and 62. It is understood and contemplated, the manner in which the foregoing incremental depression of the piston is accomplished, incorporates means for holding such setting without further involvement of the user, thereby freeing the user from continual attendance of the valve. Though the metering system has been discussed and shown in conjunction with one of the valve chambers, the present invention is not limited to such, and the metering system can be incorporated into both chambers of a symmetrical trumpet valve or incorporated into all of the chambers of a valve which has more than two chambers.

In use the present invention is highly advantageous for use in laparoscopy involving laser and/or electro-surgical probes. Accordingly, where tissue is vaporized and a plume or cloud produced within the abdominal cavity, the continuous application of incremental suction (balanced against positive pressure from insufflation of the abdominal cavity with $CO_2$ gas (pneumoperitoneum)) will provide for rapid and essentially complete evacuation of vapor from the operative field thereby ensuring unobstructive view of the operative field. In addition to the foregoing it may be desirable to provide both pistons with a metering element and associated graduations/indices on the valve. This multiple metering capability can provide the user with the ability to preset either one or both pistons to a predetermined flow/suction rate and thereby permit continuous irrigation and suction without the user's attendance to the valve.

It is to be understood that while we have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What I claim is:

1. A suction and irrigation control valve assembly for use in laparoscopic surgical procedures, comprising:

a housing defining at least one valve chamber having an elongated cylinder, said valve having an inlet and an outlet;

a piston partially disposed within said valve chamber;

manual depression means for reciprocating movement of the piston within said valve chamber upon depression anywhere from a fully open position to a fully close position; and movable metering means for adjustably positioning and setting the piston within the valve chamber a predetermined distance between said fully open and said fully close positions, and any distance therebetween, to allow at least partial communication between said inlet and said outlet, said manual depression means moving said piston within the valve chamber independently from said metering means.

2. The control valve assembly of claim 1 wherein said metering means comprises:

a gear operatively associated with the piston, the gear having at least one ramp portion;

a protruding member having a sidewall and attached above a top portion of said valve chamber, a portion of the sidewall being cutaway to define a first opening in said protruding member; and a knob having a handle portion and a circular portion, the circular portion of said knob being inserted within the cutaway of said protruding member, the handle portion of said knob having an inner surface and an outer surface, the circular portion of said knob having at least one ramp portion, the ramp portion of said gear and the ramp portion of said knob working against each other to provide retraction or extension of said piston within said valve chamber.

3. The control valve assembly of claim 2 further including at least one protrusion disposed on said housing, said protrusion being aligned with the handle portion of said knob.

4. The control valve assembly of claim 3 wherein the inner surface of said knob has a plurality of ridges or serrations, said plurality of ridges or serrations passing over the protrusion disposed on said housing to indicate a certain distance the piston has traveled within the valve chamber.

5. The control valve assembly of claim 2 wherein the outer surface of said knob has a gripping surface.

6. The control valve assembly of claim 5 wherein said gripping surface is a plurality of ridges or serrations.

7. A suction and irrigation control valve assembly for use in laparoscopic surgical procedures, comprising:

a housing defining at least one valve chamber having an elongated cylinder, at least one protrusion disposed on said housing, the valve chamber being further provided with an inlet orifice connected to a source of vacuum or irrigation fluid and a second orifice connected to a common conduit;

a piston partially disposed within said valve chamber;

manual depression means for reciprocating movement of the piston within said valve chamber, upon depression the piston having an aperture and upon reciprocating movement of the piston within the cylinder the aperture allows for communication between the orifices in said cylinder wall through the aperture;

a gear operatively associated with the piston, the gear having at least one ramp portion;

a protruding member having a sidewall and attached above a top portion of said valve chamber, a portion of the sidewall being cutaway to define a first opening in said protruding member; and a knob having a handle portion and a circular portion, the circular portion of said knob being inserted within the cutaway of said protruding member, the handle portion of said knob having an inner surface and an outer surface, the handle portion of said knob being aligned with the protrusion on said housing, the inner surface and the outer surface of said handle portion having ridges or serrations, the circular portion of said knob having at least one ramp portion, the ramp portion of said gear and the ramp portion of said knob working against each other to provide retraction or extension of said piston within said valve chamber and to adjustably position and set the piston within the valve chamber a predetermined distance between a fully open position and a fully close position, and any distance therebetween to allow at least partial communication between the inlet orifice and the second orifice of said housing said manual depression means moving said piston within the valve chamber independently from said knob and said gear.

8. An improved suction and irrigation control valve, the valve having a housing defining at least one valve chamber and an associated piston partially disposed within the valve chamber, the housing having an inlet and an outlet, the valve also having manual depression means for reciprocating movement of the piston within the valve chamber upon depression anywhere from a fully open position to a fully close position, said valve for use in laparoscopic surgical procedures, wherein the improvement comprises:

a metering device for use in conjunction with said valve, said metering device comprising:

a protruding member having a sidewall and attached above a top portion of said valve chamber, a portion of the sidewall being cutaway to define a first opening in said protruding member; and movable metering means for adjustably positioning and setting the piston within the chamber a predetermined distance between said fully open and said fully close positions, and any distance therebetween, to allow at least partial communication between said inlet and said outlet;

wherein said manual depression means moving said piston within the valve chamber independently from said metering means.

9. The metering device of claim 8 wherein said metering means comprises:

a gear operatively associated with the piston, the gear having at least one ramp portion; and a knob having a handle portion and a circular portion, the circular portion of said knob being inserted within the cutaway of said protruding member, the handle portion of said knob having an inner surface and an outer surface, the circular portion of said knob having at least one ramp portion, the ramp portion of said gear and the ramp portion of said knob working against each other to provide retraction or extension of said piston within said valve chamber.

10. The metering device of claim 9 further including at least one protrusion disposed on said housing, said protrusion being aligned with the handle portion of said knob.

11. The metering device of claim 9 wherein the inner surface of said knob has a plurality of ridges or serrations, said plurality of ridges or serrations passing over the protrusion disposed on said housing to indicate a certain distance the piston has traveled within the valve chamber.

12. The metering device of claim 9 wherein the outer surface of said knob has a gripping surface.

13. The metering device of claim 12 wherein said gripping surface is a plurality of ridges or serrations.

* * * * *